United States Patent [19]
Gutierrez et al.

[11] Patent Number: 5,885,980
[45] Date of Patent: Mar. 23, 1999

[54] COMPOSITION AND METHOD FOR TREATING DIABETES

[75] Inventors: Enrique G. Gutierrez, 5212 Wade Dr., Metairie, La. 70003; Reynold Leboeuf, Houma, La.

[73] Assignee: Enrique G. Gutierrez, Metaire, La.

[21] Appl. No.: 669,939

[22] Filed: Jun. 25, 1996

[51] Int. Cl.[6] .................... A61K 31/555; A61K 31/175
[52] U.S. Cl. ............................................ 514/186; 514/593
[58] Field of Search ..................................... 514/186, 593

[56] References Cited

U.S. PATENT DOCUMENTS

| | | | |
|---|---|---|---|
| 4,060,634 | 11/1977 | Rothe | 514/593 |
| 5,023,358 | 6/1991 | Lazaro | 556/42 |
| 5,300,496 | 4/1994 | McNeil | 514/186 |
| 5,527,790 | 6/1996 | McNeil | 514/186 |

OTHER PUBLICATIONS

Villar et al. "Effects of sulphonylureas spotaneous motility and induced contractions in rat isolated uterus" Index Medicus 87:086222, 1987.
Bankhead "Type 2 diabetes:options and optimism growing" *Medical World News*, v.30, n19, p.34, 1989.
Oral Vanadyl Sulfate Improves Insulin Sensitivity in NIDDM but Not in Obese Nondiabetic Subjects, Meyer Halberstam, Neil Cohen, Pavel Shlimovich, Luciano Rossetti, and Harry Shamoon, *Diabetes*, vol. 45, May 1996.

Improvement of Glucose Homeostasis by Oral Vanadyl or Vanadate Treatment in Diabetic Rats is Accompanied by Negative Side Effects, Jose L. Domingo, Mercedes Gomez, Juan M. Llobet, Jacinto Carbella and Carl L. Keen, *Pharmacology & Toxicology* 1991, 68, 249–253.

Perspective in Diabetes Insulin–Mimetic Effects of Vanadate Possible Implications for Future Treatment of Diabetes, Yoram Schechter, *Diabetes*, vol. 39, Jan. 1990.

Vanadium Salts as Insulin Substitutes: Mechanisms of Action, a Scientific and Therapeutic Tool in Diabetes Mellitus Research, Natesampillai Sekar, Jinping Li, and Yoram Schecter, CRC Press, Inc., 1996.

Insulin–like effect of vanadyl iion on streptozotocin–induced diabetic rats, H. Sakurai, K. Tsuchiya, M. Nukatsuka, M. Sofue and J. Kawada, *Journal of Endocrinology*, (1990) 126, 451–459.

*Primary Examiner*—Ceila Chang
*Attorney, Agent, or Firm*—Watov & Kipnes, P.C.

[57] ABSTRACT

A method of treating diabetes in a patient in need thereof, comprising administering to said patient a therapeutically effective amount of a pharmaceutically acceptable $VO^{+2}$ generating compound and a therapeutically effective amount of micronized glyburide.

11 Claims, 5 Drawing Sheets

COMPOSITION AND METHOD FOR TREATING DIABETES

FIELD OF THE INVENTION

The present invention is directed to compositions and methods of using the same for the treatment of diabetes. The composition includes a combination of the oral hypoglycemic agent micronized glyburide and a trace rare metal supplement, such as the combination of micronized glyburide and vanadyl-containing compounds.

BACKGROUND OF THE INVENTION

Vanadyl sulfate ($VOSO_4$), which is readily available over the counter in the United States at local health food stores, is marketed as a nutritional supplement. Although it is used for other purposes as well, vanadyl sulfate has been taken to improve glycemic control. Vanadyl sulfate generates the vanadyl radical ($VO^{-3}$) which has been shown to reverse diabetes in pancreatectomized rats. The radical ($VO_3^-$) is the predominate radical form in extracellular fluid. It is reduced intracellularly into the radical ($VO^{+2}$) which is the active form.

During the past ten years there has been numerous publications in the medical scientific literature demonstrating that vanadyl radical generating compounds have exceptional antidiabetic effects in animals. Vanadyl sulfate orally administered to animals has been shown to produce normoglicemia which can persist even after discontinuation of the therapy.

Efforts to reproduce the antidiabetic effect in humans have been unsuccessful. Recent published human trials show only a mild improvement in glycemic control with administration of vanadyl sulfate.

Three factors appear to hinder the efficacy of vanadyl radical generating compounds in humans. First, only small amounts (0.1–2%) of the orally administered compounds are absorbed from the human gastrointestinal tract. Most of the compound is excreted in the urine.

Another limiting factor is that vanadyl radical generating compounds exhibit limited cytoplasmic penetration. The active component of vanadyl radical generating compounds ($VO^{+2}$) is present in only very small concentrations in the intracellular compartment.

A third factor involves toxicity. Compounds which tend to have greater cellular penetration typically exhibit greater toxicity levels. In particular, vanadyl sulfate ($VOSO_4$) is $\frac{1}{10}$ as toxic than other vanadyl radical generating compounds. However, this compound has a lower antidiabetic potency than other vanadyl radical generating compounds probably due to lower cytoplasmic penetration. ($VO^{+2}$) is found in the intracellular compartment after reduction from ($VO_3^-$) commonly present in the extracellular compartment. The $VO^{+2}$ radical binds to sites located in the intracellular membrane surface inhibiting ($Na^++K^+$)—ATPase enzyme and thereby inhibiting the ($K^+$) potassium pump. This occurs in all tissues of the body.

Sulfonylureas exert hypoglycemic action and inhibit potassium channel transport by binding to proteins at the potassium channel. Of the compounds commonly known as sulfonylureas, glyburide is considered the most potent because it binds most firmly and for a longer time to the 140 kda protein at the potassium channel of all tissues of the body. Micronized glyburide or small particle glyburide is absorbed more rapidly from the gastrointestinal tract than non-micronized glyburide.

Oral hypoglycemic agents such as tolazamide, tolbutamide, chlorpropamide, micronized and non-micronized glyburide, glimepiride, glypizide, metformin, and phenformin have been available as oral treatments for diabetes, typically non-insulin dependent (Type II) diabetes. Oral hypoglycemic agents in general are disadvantageous because the extent, predictability and duration of the antidiabetic effect is unpredictable and these agents are often characterized by primary or secondary failure. Because oral hypoglycemic agents exhibit inconsistent hypoglycemic benefit, insulin therapy is preferred.

For those diabetics in which current oral medication does not offer sufficient control of their condition, insulin injections are necessary. Daily injections offer a number of risks, including hypoglycemia, wide fluctuations in glucose concentrations requiring multiple daily serum glucose determinations and multiple insulin injections, and strict dietary control which then leads to the issue of poor compliance. Other disadvantages include difficulty in self administration of an accurate dose, especially by the elderly or infirmed patients. Epidemiological data shows that over 85% of insulin treated diabetics in the United States are poorly controlled. As a result, 150 billion dollars per year is spent treating the devastating complications of the illness.

Some patients are virtually impossible to treat with insulin because their cells cannot effectively utilize or are resistant to insulin therapy. As a result of the lack of glycemic control, diabetic patients often experience a variety of conditions including: neuropathy, nephropathy, cardiomyopathy, fetinopathy, coronary and peripherovascular disease and the like. These complications occur due to the unachieved glycemic control that results from failure of the insulin, diet and/or exercise only approach.

It would therefore be a significant advance in the art of treating diabetes to provide a composition which can effectively treat both Type I and Type II diabetes and which can provide effective glycemic control for all, including patients who cannot effectively utilize or are resistant to insulin therapy or who cannot achieve desired control of serum glucose levels with an insulin, diet and/or exercise approach. It would be a further advance in the art to provide such a composition in oral dosage form to ease the burden on patients who have been subjected to daily insulin injections and monitoring.

SUMMARY OF THE INVENTION

The present invention is directed to a composition and method for the treatment of Type I and Type II diabetes and complications arising therefrom comprising a therapeutically effective amount of each of:

a) a $VO^{+2}$ generating compound; and b) micronized glyburide.

The present invention is also directed to a method of treating diabetes comprising administering to a warm blooded animal, including humans, a therapeutically effective amount of the composition of the present invention.

BRIEF DESCRIPTION OF THE DRAWINGS

The following drawings are illustrative of embodiments of the invention and are not intended to limit the scope of the invention as encompassed by the claims forming part of the application.

DETAILED DESCRIPTION OF THE INVENTION

Figure 1:
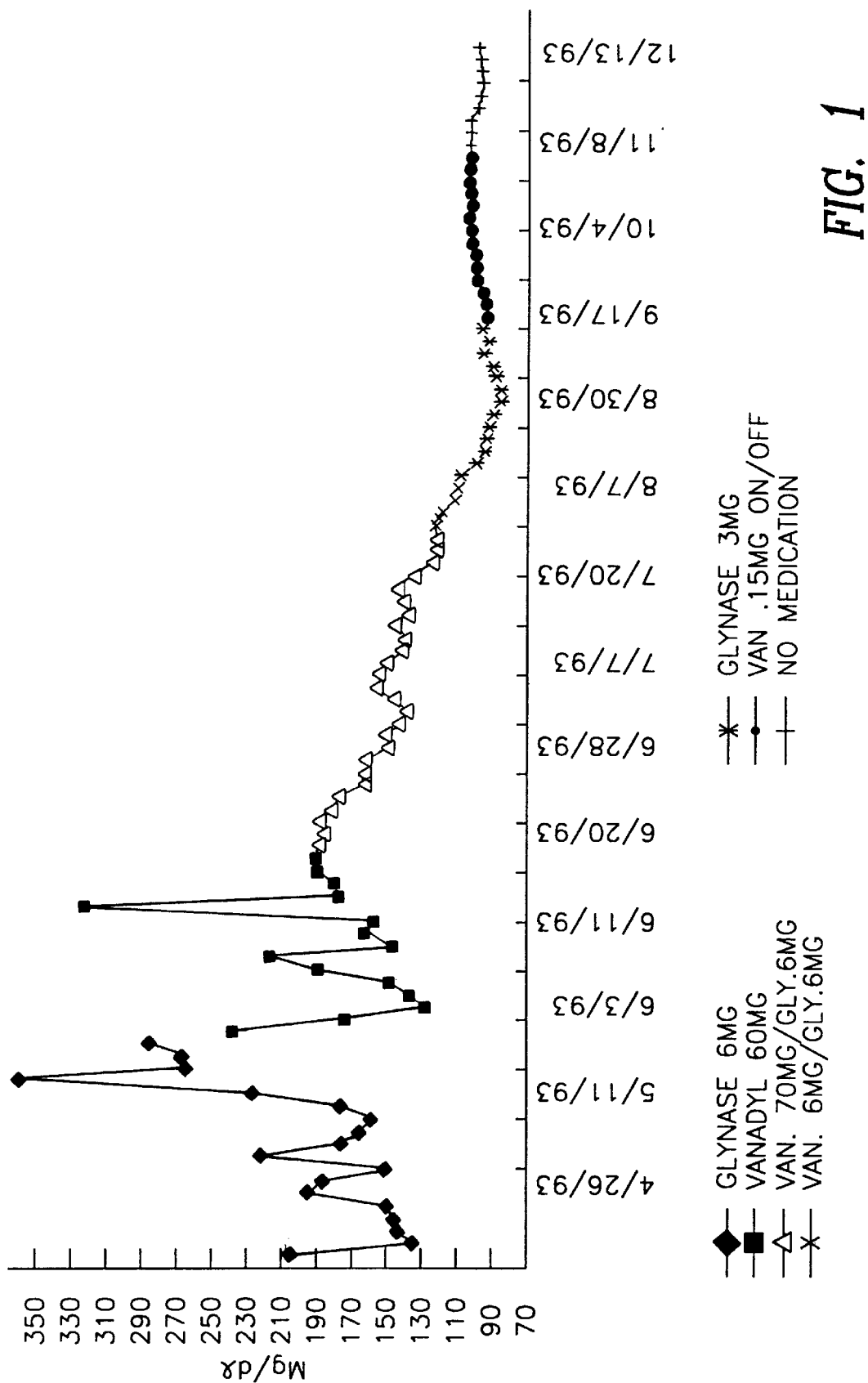
FIG. 1 is a graph showing glucose levels for the treatment of a Type II adult onset diabetic patient using Glynase (micronized glyburide) alone, vanadyl sulfate alone and the composition of the present invention.

The present invention is directed to a composition and method of treating warm blooded animals, including humans suffering from diabetes with a pharmaceutical composition comprising a $VO^{+2}$ generating compound together with micronized glyburide as the active agents. The active agents may be administered together or separately so long as the active agents can coact in the body to achieve the desired effect. It is preferred that the active agents be administered together, and most preferably in a single formulation. If administered separately, administration is preferably conducted at or about the same time.

As used herein the term "$VO^{+2}$ generating compound or vanadyl compound" shall mean any compound which forms the radical ($VO^{+2}$) in the body (e.g. which releases he same when intracellularly administered to a warm blooded animal). Examples of vanadyl compounds include sodium orthovanadate, sodium metavanadate, bis oxovanadium, sodium metavanadate ($NaVO_3$), vanadyl sulfate ($VOSO_4$), sodium orthovanadate ($Na_3VO_4$), ammonium metavanadate ($NH_4VO_3^-$), aluminum orthophosphate vanadia ($V_2O_5$–$AlPO_4$), diperoxovanadate, bis(maltolato)oxovanadium(IV) (BMOV), $VOCl_3$, $VOCl_{21}$ $VCl_3$, peroxovanadium(pv) compounds, $K_2[VO(O_2)_2$ (picolinato)] $2H_2O)[bpv(pic)]$ $VO(O_2)(picolinato)(H_2O)2[MPV(pic)]$ and the like.

As previously indicated, the $VO^{-3}$ radical is reduced after entry into the cells into the radical $VO^{+2}$. Because the element vanadium readily changes oxidation state, it is preferred to describe the therapeutic amounts of $VO^{+2}$ generating compounds on the basis of the weight of the element vanadium. The preferred $VO^{+2}$ generating compound is vanadyl sulfate in part because it is considered least toxic.

The amount of the $VO^{+2}$ radical necessary to obtain the desired results in accordance with the present invention is generally in the range of from about 5 to 60 mg/day for humans, preferably from about 20 to 35 mg/day. When administered in the form of a $VO^{+2}$ generating compound, the amount of the compound necessary to obtain the desired amount of the $VO^{+2}$ radical can be readily calculated. By way of example, vanadyl sulfate ($VOSO_4$) can generally be administered in an amount of from about 10 to 120 mg/day, preferably from about 30 to 90 mg/day, most preferably from about 60 to 90 mg/day. Vanadyl sulfate is commercially available as a nutritional supplement from several sources including GNC health food stores. The required dosage amount may be administered once or up to several times a day, preferably once a day.

It should be understood that micronized glyburide is representative of members of the sulfonylurea family which comprise the second active agent of the present invention. These compounds lower blood glucose by stimulating the release of insulin from the pancreas initially when therapy is begun then later normalize glucose via unknown extrapancreatic or peripheral effects.

Micronized glyburide or small particle glyburide is administered in accordance with the present invention in an amount of from about 0.75 to 12 mg/day, preferably from about 1.25 to 9 mg/day, most preferably from about 1.5 to 7.5 mg/day. Micronized glyburide is currently available from UpJohn under the name Glynase™ PresTabs™ and as a generic product by Coply. Micronized glyburide may be administered in accordance with the present invention as a single dose or up to four times daily, preferably in one dose with the vanadyl radical generating compound as previously described.

The active ingredients of the present invention are administered orally in the form of tablets, capsules, caplets, soft gel capsules and the like. The amount of each active ingredient which is administered per day will depend on the extent of the patient's condition as determined by the extent of the loss of glycemic control. Assessment of insulin resistance can be achieved by clinical observation of its manifestations such as hirsutism, hyperpigmentation, and acne in women. It can also be measured by performing a glucose tolerance test with concomitant measurements of serum glucose and insulin concentrations.

Assessment of glycemic control can be achieved through monitoring serum glucose concentrations, fasting and postprandial as well as measuring glycohemoglobin and fructosamine and through the use of a glucose tolerance test.

For example, a typical daily dosage of vanadyl sulfate and micronized glyburide based on the extent of loss of glycemic control or for insulin resistance for a typical patient is set forth in Table 1.

TABLE 1

| Extent of Disease | Amount of Micronized Glyburide | Amount of Vanadyl Sulfate | Weight ratio Vanadyl Sulate:Glyburide |
|---|---|---|---|
| mild | 1.5–3 mg | 40 mg | 26.6:1 |
| moderate | 3–9 mg | 40–60 mg | 13:1–20:1 |
| severe | 6–12 mg | 60–120 mg | 5:1–40:1 |

The combination of the $VO^{+2}$ generating compound and micronized glyburide is generally administered over a period of from about 2 weeks to 6 months, preferably from about 3 to 14 weeks, most preferably from about 4 to 12 weeks. During the period of administration the total amount of the $VO^{+2}$ generating compound (e.g. vanadyl sulfate) administered is generally from about 1000 to 3000 mg. Shorter or longer durations of treatment can be employed depending on patient response. Once response is achieved it can be administered indefinitely without any significant adverse or side effects.

In a preferred form of the invention for the treatment of diabetes a dosage of 60–90 mg of vanadyl sulfate and 6–12mg of micronized glyburide are administered once daily, preferably in the morning for at least 8 weeks and up to 20 weeks until a response is noted with stabilization of serum glucose concentrations at the normal or near normal ranges. Thereafter, the dosage regimen is reduced to 6 mg of glyburide/60 mg of vanadyl sulfate administration. Glycemic control is achieved independently of insulin production.

The active components (e.g. vanadyl sulfate and micronized glyburide) are commercially available and can be utilized as such in the present invention. However, if fixed combination dosages forms are desired, they may be formulated by grinding each of the commercially available components together and placing the appropriate amount of the combination in an appropriate dosage delivery form (e.g. capsule or tablet) by known techniques. Alternatively, the active components may be optionally mixed along with pharmaceutically acceptable carriers (e.g. cornstarch, lactose, lecithin, soybean oil, glycerine and the like) as desired, and the mixture put up into an appropriate dosage form according to known techniques in the art. Ideally a tablet containing 3 mg glyburide and 30 mg vanadyl sulfate would be most practical for this purpose.

The active components are commercially available in bulk form or may also be prepared by known methods. Glyburide can be prepared in accordance with published Netherland Patent Application 66/03,398; C.A. 66/65,289h (1967); Aumuller et al., Arzneimettel-Forsch. 16, 1640 (1966); and Belgian Patent 730,791 each of which is incorporated herein by reference. Additional details about micronized glyburide can be found in U.S. Pat. Nos. 4,916,163 and 4,735,805, each of which is also incorporated herein by reference.

The following examples are submitted to illustrate embodiments of the invention and are not intended to limit the invention as encompassed by the claims forming part of the application.

EXAMPLE 1

A 57 year old smoker was diagnosed with diabetes in 1992. He had concurrent severe coronary artery disease which required angioplasty several years prior to 1992. As shown in FIG. 1, the subject was taking 6 mg of Glynase. However, glucose levels were poorly controlled ranging from a low of 130 mg/dl to a high of above 350 mg/dl. Glynase administration was stopped followed by administration of vanadyl sulfate at a daily dosage of 60 mg. As shown in FIG. 1, glucose levels were slightly improved but nonetheless glucose levels were sporadic ranging from about 120 to 320 mg/dl.

Thereafter, the subject received 60 mg of vanadyl sulfate and 6 mg of Glynase per day for a period of approximately one month. There was an immediate and significant reduction in both the level of serum glucose concentrations of the subject and the degree of serum glucose fluctuations.

Thereafter for a period of approximately one week, the amount of vanadyl sulfate was increased to 70 mg per day and there was a further drop of glucose level to approximately 110 mg/dl. The subject discontinued the composition in accordance with the present invention and was placed on Glynase 3mg for approximately six weeks. The level of glucose remained in the desirable range of from about 90 to 110 mg/dl. Glynase therapy was discontinued and the subject was placed on 15 mg of vanadyl sulfate per day with glucose levels remaining below about 110 mg/dl. Thereafter all medication was discontinued and the patient maintained normal glucose levels (e.g. between 90 and 110 mg/dl) independently. 8 months after discontinuing the therapy the patient's glycohemoglobin or HgbAic was 5.5% (non-diabetic 3–6%; good control 6–9%. The patient was not following a diet or exercise regimen during this time and his weight remained stable. This suggests the treatment may have arrested and reversed the illness.

As shown with the subject discussed in Example 1, the combination of vanadyl sulfate and Glynase resulted in a significant lowering of glucose levels and maintenance of glucose levels within a narrow, normal range. In this case this effect persisted indefinitely even after discontinuing the therapy.

EXAMPLE 2

Figure 2:
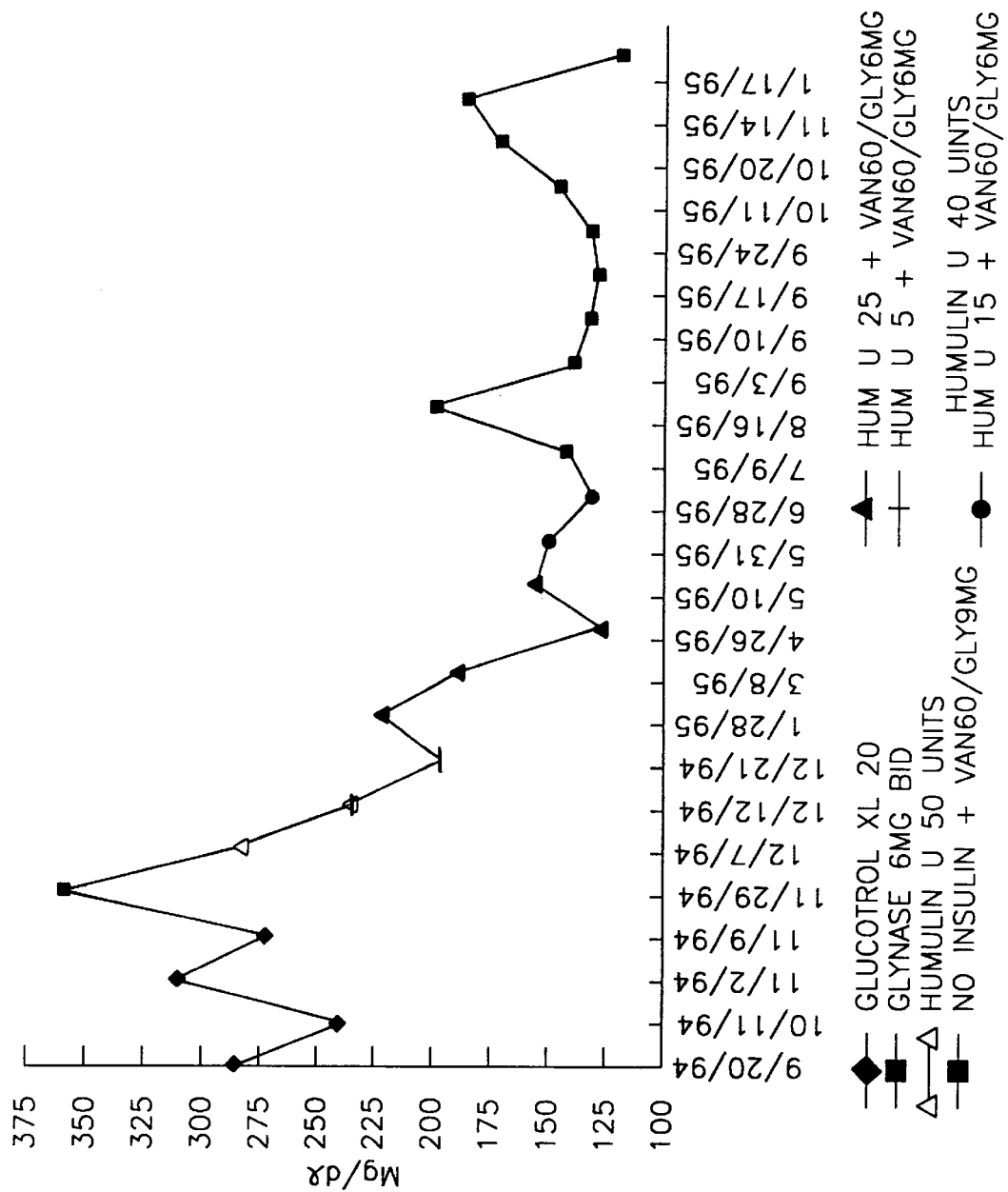
FIG. 2 is a graph showing glucose levels for the treatment of a Type II insulin dependent diabetic in poor control using insulin alone and a composition of the present invention.

A 59 year old black female had a seven year history of diabetes mellitus. When the subject was first tested as shown in FIG. 2, she was taking glucotrol (20 mg) which is an anti-diabetic oral medication. As shown in FIG. 2, glucose levels were high and sporadic in the range of 235 to 360 mg/dl. Thereafter for short periods of time the subject took Glynase 6 mg twice a day followed by 40 units of insulin per day followed by 50 units of insulin per day over the course of about 1 year. As a result, glucose levels were reduced to as low as 200 but still remained unacceptably high. The subject's glycohemoglobin level also rose to greater than 10%.

Thereafter, the patient was administered 25 units of insulin per day plus 60 mg of vanadyl sulfate and 6 mg of Glynase over the course of approximately 6 months. Glucose levels dropped from a high of about 215 mg/dl to a low of about 125 mg/dl during this therapy.

Thereafter, insulin therapy was discontinued but the subject continued to receive 60 mg of vanadyl sulfate with 9 mg of generic Glynase per day. As a result, the subject's glucose levels remained at the lowest levels previously achieved (e.g. about 135 mg/dl) and at the end of the test was actually below about 125 mg/dl. The subject has remained off insulin for almost one year while maintaining a hemoglobin AIC level of around 7.0 which reflects excellent control.

EXAMPLE 3

A 14 year old white female was diagnosed with Type I juvenile insulin dependent diabetes mellitus at the age of 11. From the age of 11 to 13 she exhibited poorly controlled glucose levels with glycohemoglobins above 10 and as high as 14. Her doctor had classified her as being a brittle diabetic.

Figure 3:
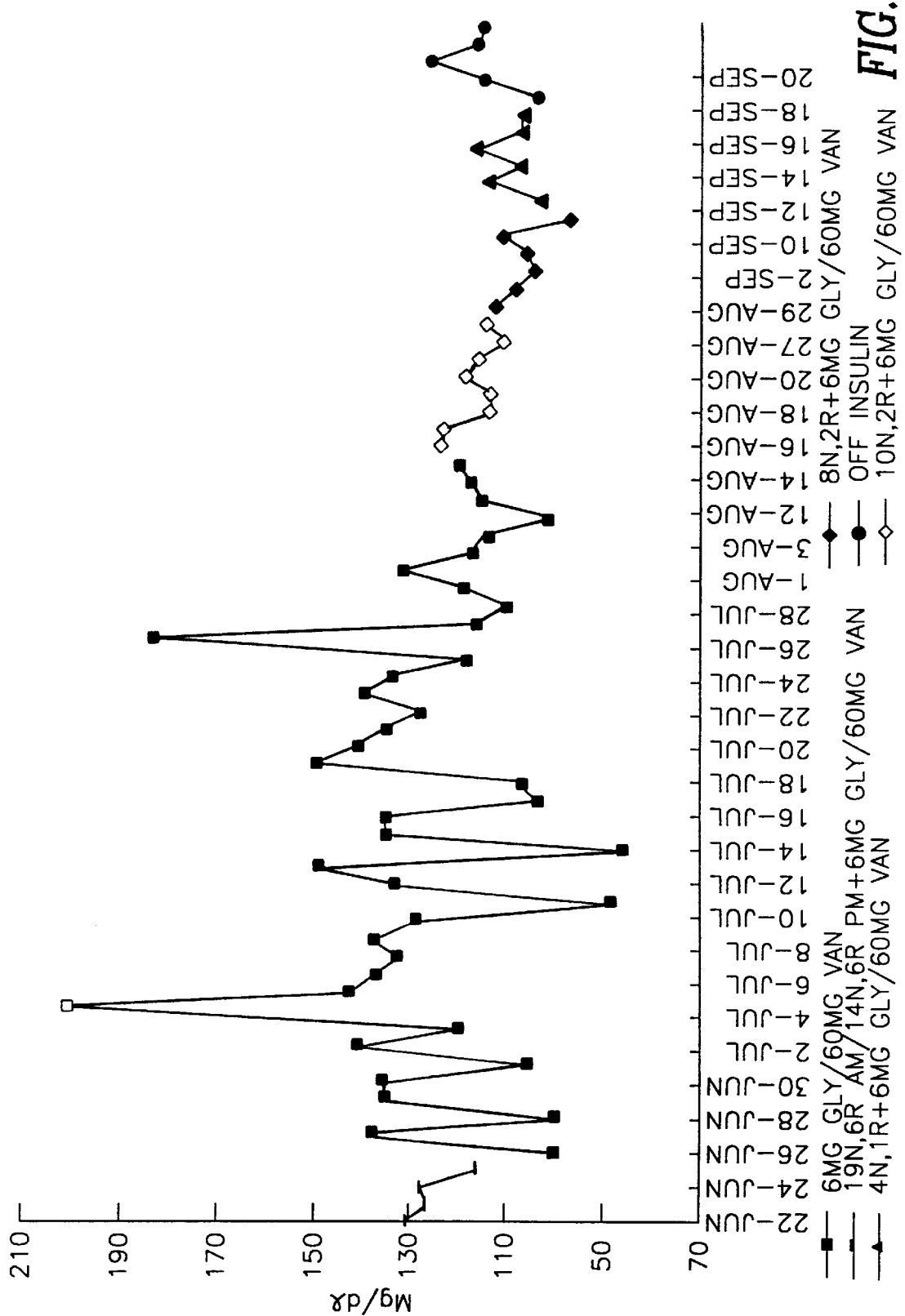
FIG. 3 is a graph showing glucose levels for the treatment of a Type I juvenile diabetic in poor control with insulin alone and with a composition of the present invention.

As shown in FIG. 3, the subject was receiving 25 units of insulin in the morning and 20 units of insulin in the evening as per established therapy. Thereafter, insulin administration was continued and the combination of 60 mg vanadyl sulfate and 6 mg of Glynase was added to the insulin therapy administered daily over the course of approximately 6 weeks. Initially the subject's glucose levels were very erratic ranging from a low of 80 to a high of about 200 mg/dl. However, after about 4 weeks of therapy, glucose levels began to stabilize from a high of about 160 to a low of about 100 mg/dl.

Thereafter, vanadyl sulfate/Glynase therapy was continued and insulin therapy was reduced, first to 12 units per day, then to 10 units per day and finally to 5 units per day. During this course of lower insulin therapy, glucose levels became stabilized in or about the range of 110 mg/dl. Thereafter, insulin therapy was discontinued and after an initial uptake in glucose levels, the glucose levels began to stabilize at about 110 mg/dl.

The subject of Example 3 was able to come off insulin and maintain normal, consistent glucose levels without insulin administration after administration of the composition of the present invention.

EXAMPLE 4

A 77 year old white male was diagnosed with insulin dependent diabetes mellitus. He was considered to be a brittle diabetic. He had extreme difficulty with frequent hypoglycemic events where blood sugar levels would drop to below 20 mg/dl as often as two or three times weekly. This happened for approximately 10 years in spite of many different treatments employing insulin therapy.

Figure 4:
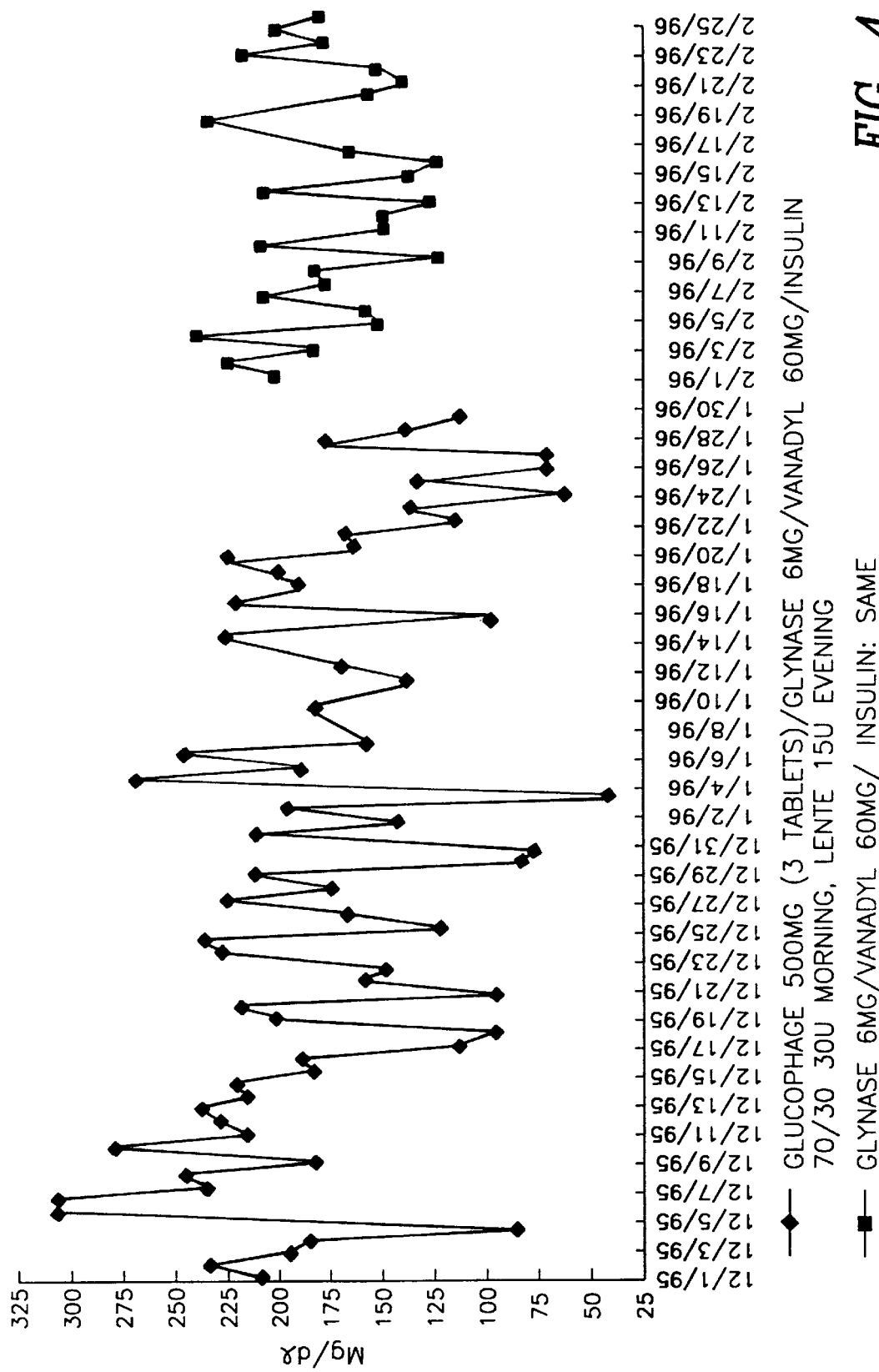
FIG. 4 is a graph showing glucose levels for the treatment of a Type II difficult to control diabetic with a history of unusual high frequency of hypoglycemic events with insulin and the composition of the present invention.

As shown in FIG. 4, the subject received 500 mg of glucophage, a known oral anti-diabetic drug as well as 6 mg of Glynase and 60 mg of vanadyl sulfate along with insulin with 30 units in the morning and 15 units in the evening in an effort to stabilize the serum glucose levels.

The subject's glucose levels remained high and erratic over the course of the therapy but he stopped having hypoglycemic induced comas. After approximately two months glucophage was eliminated from the therapy. There was a noticeable further improvement in both the glucose level and the changes in glucose levels from day to day.

EXAMPLE 5

A 42 year old black female developed type I juvenile insulin dependent diabetes at age 8. Over the years she developed progressively greater insulin resistance (acanthosis nigricans).

Figure 5:
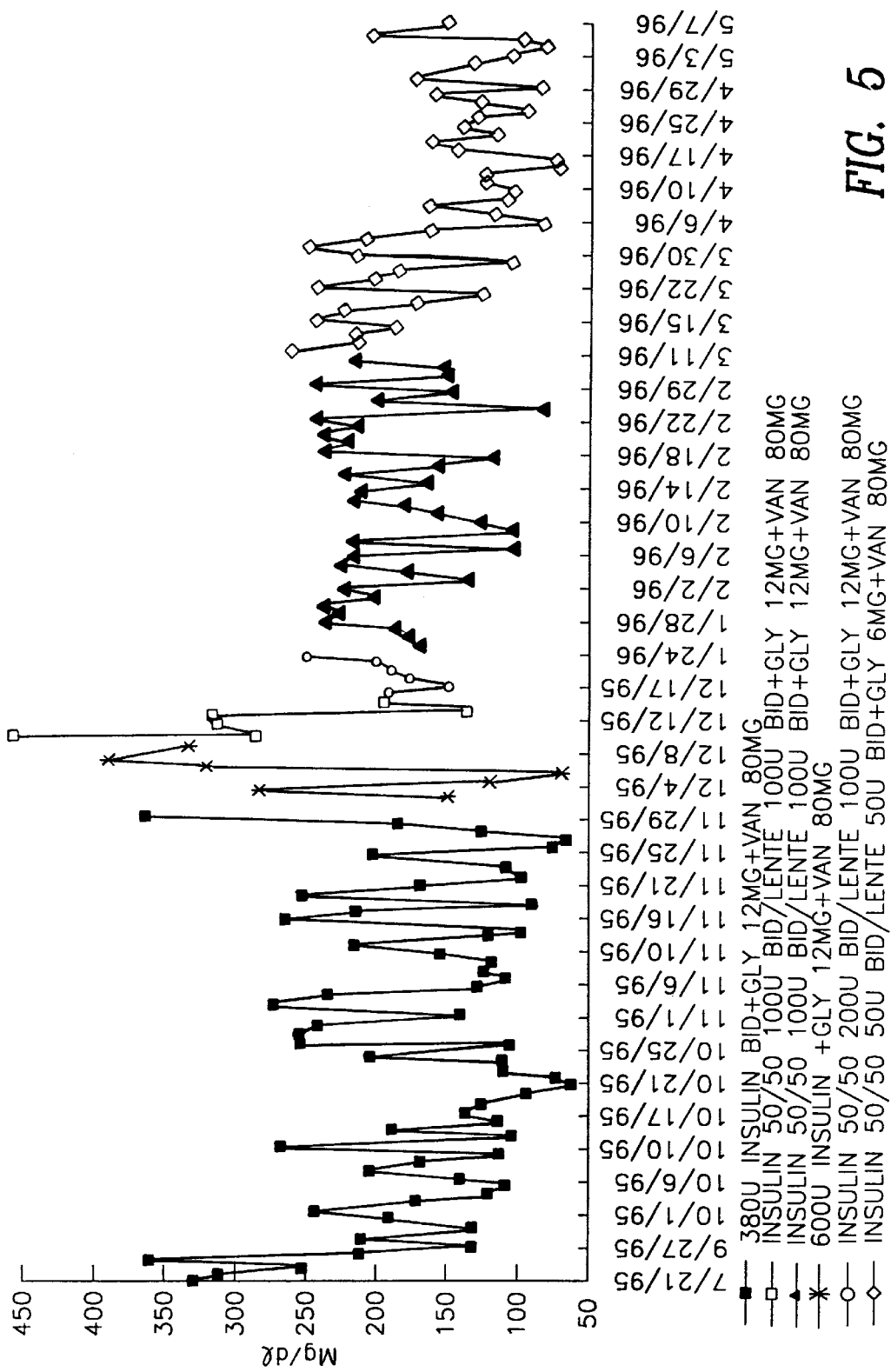
FIG. 5 is a graph showing glucose levels for the treatment of a Type I diabetic with acanthosis nigricans and severe insulin resistance with no glycemic control and who is unresponsive to insulin therapy, with insulin alone and in combination with the present invention.

In 1980 she was hospitalized in the intensive care unit. She was administered up to 1,200 units of insulin daily without success. She was then classified as an untreatable diabetic. As shown in FIG. 5, she experienced erratic and elevated serum glucose levels in spite of extremely high doses of insulin (around 800 units daily) and maximal doses of Glynase 12mg daily. The subject also took 24 mg of Glynase daily for several months without success.

Thereafter the subject received both vanadyl sulfate (80 mg) and Glynase (12 mg) which reduced the daily insulin requirement to only 200 units from 1,200 and furthermore stabilized glycemic control. The stabilization of her glycemic control was confirmed by a glycohemoglobin—HgbAic of 8.9% in the controlled diabetic range. Prior to this therapy her glycohemoglobins were always in the poor control range ≧10.

The subject also had several fructosamine tests over the two months of good control which were in the normal range confirming good control.

These fructosamines, glycohemoglobin, serum glucose measurements establish that the patient possessed glycemic control.

We claim:

1. A pharmaceutical composition for use in the treatment of diabetes, said composition comprising a therapeutically effective amount of:

(a) $VO^{+2}$ generating compound selected from the group consisting of sodium orthovanadate, sodium metavanadate, bis oxovanadium, sodium metavanadate ($NaVO_3$), vanadyl sulfate ($VOSO_4$), sodium orthovanadate ($Na_3VO_4$), ammonium metavanadate ($NH_4VO_3$), aluminum orthophosphate vanadia ($V_2O_5AlPO_4$), diperoxovanadate, bis (maltolato) oxovanadium (IV) (BMOV), $VOCl_3$, $VOCl_2$, $VCl3$, peroxovanadium (pv) compounds, $K_2[VO(O_2)_2$ (picolinato)]($2H_2O$) [bpv(pic)], and $VO(O_2)$ (picolinato) ($H_2O$)2[MPV(pic)] said $VO^{+2}$generating compound providing from about 5 to 60 mg/day of the $VO^{+2}$ radical; and (b) micronized glyburide in an amount of from about 0.75 to 12 mg/day.

2. The pharmaceutical composition of claim 1 wherein said $VO^{+2}$ generating compound is vanadyl sulfate.

3. The pharmaceutical composition of claim 1 wherein said effective amount of the $VO^{+2}$ generating compound is from about 10 mg to 120 mg per day.

4. The pharmaceutical composition of claim 1 wherein the $VO^{+2}$ generating compound is vanadyl sulfate and said effective amount is from about 60 to 90 mg per day and the amount of said micronized glyburide is from about 1.25 to 9 mg per day.

5. A method of treating diabetes in a warm blooded animal, comprising administering to said patient a therapeutically effective amount of the composition according to claim 1.

6. The method of claim 1 wherein the warm blooded animal is a human being.

7. The method of claim 6 wherein said $VO^{+2}$ compound is vanadyl sulfate.

8. The method of claim 5 further comprising administering said composition daily for a period of from about 3 to about 14 weeks.

9. A method of treating an insulin-resistant related condition in a patient in need thereof, comprising administering to said patient a therapeutically effective amount of the pharmaceutical composition according to claim 1.

10. The method of claim 9 wherein the $VO^{+2}$ generating compound is vanadyl sulfate.

11. The method of claim 9 wherein said treatment comprises administering to said patient, said composition containing from about 10 to 120 mg of vanadyl sulfate per day and from about 0.75 to 12 mg of micronized glyburide per day.

* * * * *